United States Patent [19]

Sakura et al.

[11] Patent Number: 4,943,553

[45] Date of Patent: Jul. 24, 1990

[54] METHOD OF MAKING ETHYLBIPHENYLS

[75] Inventors: Kathuhiko Sakura, Tokyo; Genki Takeuchi, Kitakyushu; Naoko Takeshita, Yukuhashi, all of Japan

[73] Assignee: Nippon Steel Chemical Co., Ltd., Tokyo, Japan

[21] Appl. No.: 432,416

[22] Filed: Nov. 2, 1989

Related U.S. Application Data

[63] Continuation of Ser. No. 210,964, Jun. 24, 1988, abandoned.

[51] Int. Cl.$^5$ ............................................. C07C 15/12
[52] U.S. Cl. ................................. 585/471; 585/474; 585/475
[58] Field of Search ................. 585/471, 472, 474, 475

[56] References Cited

U.S. PATENT DOCUMENTS

| | | | |
|---|---|---|---|
| 2,744,150 | 5/1956 | Enos | 585/472 |
| 3,410,921 | 11/1968 | Pollitler | 585/471 |
| 3,636,179 | 1/1972 | Inoue et al. | 260/68 |
| 3,701,813 | 10/1972 | Stenmark | 585/472 |
| 3,716,596 | 2/1973 | Bowes | 585/455 X |
| 3,855,328 | 12/1974 | Hedge | 585/471 |
| 4,112,056 | 9/1978 | Chen | 502/77 X |
| 4,454,364 | 6/1984 | Farcasiu et al. | 585/472 |
| 4,547,474 | 10/1985 | Olah | 585/474 |
| 4,642,730 | 2/1987 | Sato et al. | 585/471 |

FOREIGN PATENT DOCUMENTS

| | | | |
|---|---|---|---|
| 0202752 | 11/1986 | European Pat. Off. | |
| 1350893 | 4/1974 | Japan | |
| 0116353 | 10/1978 | Japan | 585/472 |
| 56-156222 | 12/1981 | Japan | |
| 2252733 | 11/1987 | Japan | 585/474 |

OTHER PUBLICATIONS

Chemical Abstracts, vol. 108, No. 13, abstract number 111947g, 1988.

*Primary Examiner*—Patrick P. Garvin
*Assistant Examiner*—George R. Fourson
*Attorney, Agent, or Firm*—Armstrong, Nikaido, Marmelstein, Kubovcik & Murray

[57] ABSTRACT

This invention relates to a method of making ethylbiphenyls by the reaction of biphenyl with polyethylbenzenes or with ethylene and polyethylbenzenes in the presence of a solid acid catalyst and offers advantages of industrial significance such as absence of acidic waste water, no need of costly materials for equipment, catalyst reuse, and adaptability to a fixed-bed flow reaction system suitable for large-scale production.

16 Claims, 1 Drawing Sheet

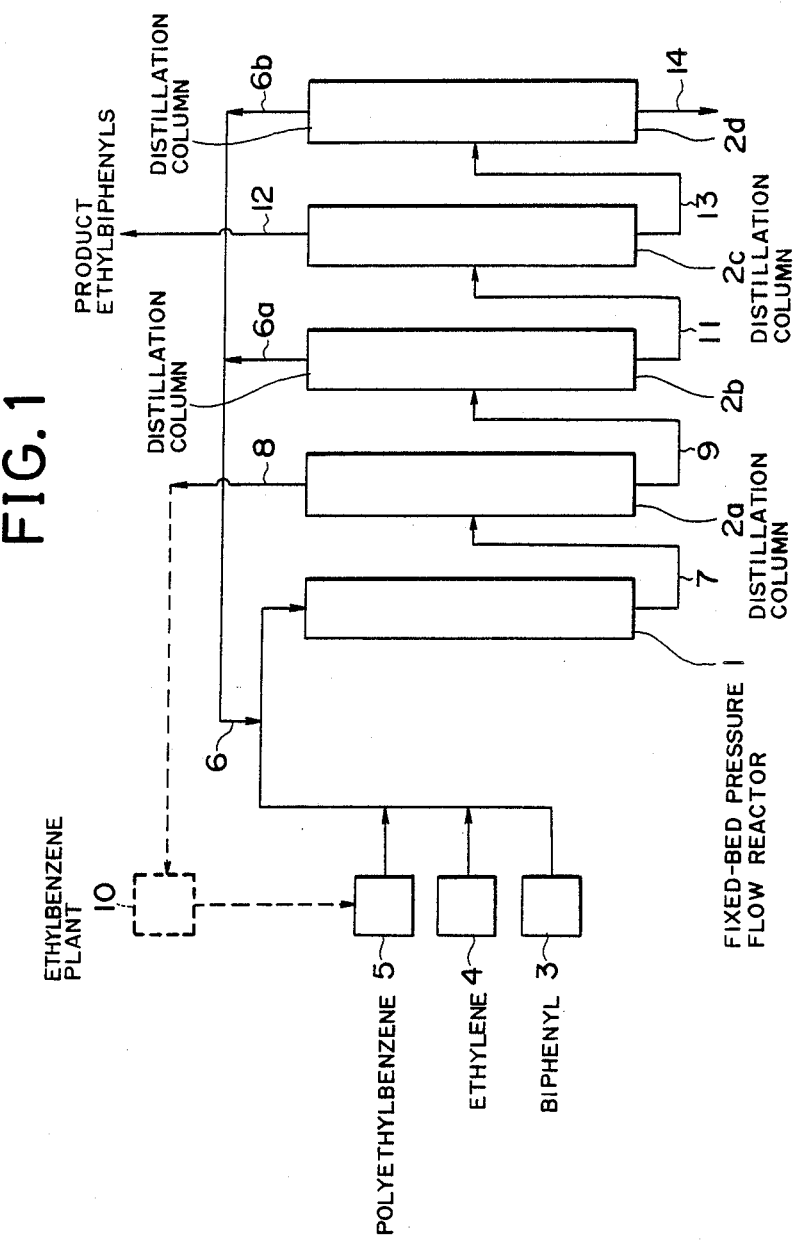

METHOD OF MAKING ETHYLBIPHENYLS

This application is a continuation of application Ser. No. 210,964, filed Jun. 24, 1988, now abandoned.

FIELD OF THE INVENTION AND RELATED ART STATEMENT

This invention relates to a method of making ethylbiphenyls which are useful as heat transfer fluids.

Ethylbiphenyls are made by the ethylation of biphenyl; for example, Japanese Patent Publication No. 15,945-1972(U.S. Pat. No. 3,636,179) discloses a method of making ethylbiphenyls by the catalytic transalkylation of biphenyl and ethylated benzenes containing ethylbenzenes, diethylbenzenes, triethylbenzenes, and tetraethylbenzenes in the presence of $AlCl_3$.

The Friedel-Crafts reaction using $AlCl_3$, however, generally possesses the following defects:

(1) The step for water washing and neutralization are required for the removal of $AlCl_3$ upon completion of the reaction, and acidic waste water is generated in large quantities;

(2) The reaction equipment must be made acid-resistant;

(3) The reaction is hard to carry out on a continuous basis; and (4) The reuse of the spent $AlCl_3$ is difficult. The aforesaid method is no exception in this respect.

Another method in Japanese Kokai Document Nos. 156,222-1981 and 1,869-1972 (GB Patent No. 1,350,893) described the manufacture of ethylbiphenyls by the reaction of biphenyl with ethylene in the presence of a solid acid catalyst. It is, however, not readily applicable on an industrial scale because such solid acid catatlyst has a short life and the methods are difficult to practice in a fixed-bed flow reactor.

OBJECT AND SUMMARY OF THE INVENTION

The present inventors have conducted studies in search of remedies to the aforesaid defects, found that solid acid catalysts can be as reactive as $AlCl_3$ and yet free of the shortcomings of $AlCl_3$, and completed this invention.

An object of this invention is to provide a method of making ethylbiphenyls which as effective as the Friedel-Crafts reaction using the conventional $AlCl_3$ catalyst, generates no acidic waste water, requires no costly materials for the reaction equipment, and uses reusable catalysts of long life.

Another object of this invention is to provide a method of making ethylbiphenyls which can be practiced on a continuous basis in a fixed-bed flow reactor.

Still another object of this invention is to provide a method of making ethylbiphenyls which prolongs the life of a solid acid catalyst to an industrially viable extent by the transethylation of biphenyl or by a combination of the ethylation and transethylation of biphenyl in the presence of such solid acid catalyst.

This invention thus relates to a method of making ethylbiphenyls which uses a solid acid as catalyst to the ethylation of biphenyl with polyethylbenzenes or with ethylene and polyethylbenzenes.

The solid acid catalysts useful for this invention include silica-alumina, zeolites such as mordenite and Y zeolite, sulfate ions on metal oxide carriers, heteropoly acids, and ion exchange resins, all generally known as exceedingly strong solid acids. Consideration of reactivity, commercial availability, and minimal production of thermally unstable byproducts favors silica-alumina and zeolites or their mixtures. The catalysts should preferably have from 0.1 mole to 3 moles of acid sites per kg, each mole of the acid sites showing heat of adsorption of ammonia of 85 kilojoules or more. Industrially sufficient conversion is difficult to obtain with acid sites of 0.1 kg or less while carbonaceous deposits form faster and the catalyst loses its activity faster with acid sites of 3 moles per kg or more.

The reaction temperature is set in the range of from 130° to 380° C., preferably from 150° to 350° C., and more preferbly from 200° to 320° C. Secondary reactions begin to accompany the ethylation above 380° C. while the conversion is not sufficiently high below 130° C.

The reaction pressure is from ambient to 30 $kg/cm^2$.G, preferably from 2 to 20 $kg/cm^2$.G. A pressure above 30 $kg/cm^2$.G is allowable, but is not necessary.

The optimal reaction time or contact time varies with the reaction temperature chosen. A batch reaction should preferably run from 1 to 3 hours, and a continuous reaction should preferably run a weight hourly space velocity of from 0.5 to 3 kg/kg.hr. An unnecessarily long reaction time will cause the undesirable deethylation of the reaction products.

The quantity of feed polyethylbenzenes in the production of monoethylbiphenyls is chosen so that from 0.3 to 4 moles, preferably from 0.5 to 2 moles of the ethyl group or (ethyl group+ethylene) is present per each mole of (biphenyl ring+benzene ring). More biphenyl would remain unchanged if this mole ratio fell below 0.3 while less monoethylbiphenyls and more polyethylbiphenyls would form if the ratio exceeded 4. In the cases where the intended product is diethylbiphenyls or higher polyethyldiphenyls, from 1 to 4 moles, preferably from 1.5 to 3 moles of the ethyl group or (ethyl group+ethylene) should be present per each mole of (biphenyl ring+benzene ring). Moreover, when polyethylbiphenyls produced are returned to a reaction system, the ethyl groups and biphenyls thereof are taken into account as well.

It is desirable for the feed polyethylbenzenes to contain from 1.5 to 4 moles, preferably from 2 to 3 moles, of the ethyl group per mole of benzene ring. When a mixed feed of polyethylbenzenes and ethylene is used, it is desirable that 2 moles or less, preferably from 0.2 to 1 mole, of ethylene is present for each mole of the ethyl group in the polyethylbenzenes. A larger quantity of ethylene forms more carbonaceous deposits on the catalyst and shortens the catalyst life.

The method of this invention can be practiced in a flow or batch mode. A fixed-bed flow reactor is suitable for large-scale production and a batch reactor for small-scale one. In either case, the catalyst can be separated readily from the reaction products. The reaction equipment may be constructed of stainless steel equivalent to SUS 304 and requires no acid-resistant glass lining.

When the reaction is carried out batch-wise, the spent catalyst separated after the reaction is reused with or without regeneration in the usual manner by firing at 500° C. or so in a stream of air diluted with nitrogen.

On the other hand, in a continuous operation using a fixed-bed flow reactor, plural reactors are provided in parallel between the feed line and the product line; as soon as the catalyst in one of the reactors is deactivated, the process flow is switched to another reactor containing fresh catalyst, the spent catalyst is regenerated or replaced and used again when the fresh catalyst in turn loses its activity. The product line is connected to a distillation column, preferably several in series, and the products withdrawn from the reactor are continuously separated and purified into the product ethylbiphenyls. The biphenyl and polyethylbenzenes recovered unchanged and polyethylbiphenyls produced are returned to the reactors as recycle feed.

The method of this invention for making ethylbiphenyls with the use of solid acid catalysts differs markedly from the conventional method using the AlCl₃ catalyst and offers advantages of industrial significance in that it generates no acidic waste water, requires no costly construction material for the equipment, and permits reuse of the catalyst.

BRIEF DESCRIPTION OF THE DRAWING

FIG. 1 is the flowsheet for Example 7 in which ethylbiphenyls are manufactured continuously in a flow reactor embodying the method of this invention.

ing biphenyl ring in the reaction products is shown in Table 2.

The polyethylbenzenes used as feed were by-products in the manufacture of ethylbenzene.

TABLE 1

|  | BP (Parts by weight) | PEB (Parts by weight) | Catalyst (Parts by weight) | Et Group/ (BPR + BR) Mole Ratio | Reaction Temperature (°C.) | Reaction Time (h) | Reaction Pressure (kg/cm² · G) |
|---|---|---|---|---|---|---|---|
| Example 1 | 92.4 | 160.9 | 40 | 1.07 | 250 | 2 | 3 |
| Example 2 | 107.8 | 117.3 | 40 | 0.89 | 300 | 2 | 10 |
| Example 3 | 92.4 | 160.9 | 40 | 1.07 | 300 | 2 | 10 |
| Example 4 | 38.5 | 134.0 | 40 | 1.28 | 300 | 2 | 10 |

BP: Biphenyl
PEB: Polyethylbenzene
BPB: Biphenyl ring
BR: Benzene ring.

TABLE 2

|  | BP (wt %) | EBP (wt %) | | | DiEBP (wt %) | TrEBP (wt %) | TeEBP (wt %) | 9-MF (wt %) | Othersrts (wt %) | Total (wt %) |
|---|---|---|---|---|---|---|---|---|---|---|
|  |  | meta | para | Subtotal |  |  |  |  |  |  |
| Example 1 | 35.6 | 14.8 | 29.2 | 44.0 | 12.2 | 4.1 | 0.8 | 1.0 | 2.2 | 100 |
| Example 2 | 31.0 | 26.4 | 16.4 | 42.8 | 10.9 | 6.4 | 1.1 | 7.1 | 0.7 | 100 |
| Example 3 | 18.5 | 22.0 | 14.1 | 36.1 | 19.7 | 11.9 | 6.6 | 5.9 | 1.2 | 100 |
| Example 4 | 12.4 | 18.1 | 13.2 | 31.3 | 23.4 | 15.5 | 11.1 | 4.0 | 2.3 | 100 |

EBP: Ethylbiphenyls
DiEBP: Diethylbiphenyls
TrEBP: Triethylbiphenyls
TeEBP: Tetraethylbiphenyls
9-MF: 9-Methylfluorene.

COMPARATIVE EXAMPLE 1

The reaction was carried out as in Examples 1~4 with the use of AlCl₃ as catalyst. The reaction conditions and the results are shown in Table 1 and 2 respectively.

EXAMPLE 5

A fixed-bed pressure flow reactor was filled with Y zeolite (acid sites, 1.19 mole per kg) and a mixture of biphenyl and diethylbenzenes at a mole ratio of 1:4 was fed at 250° C. and a liquid hourly space velocity of 1 1/l. hr. The effluents from the reactor accumulated over a period from the 24th to 32nd hour and those from 64th to 72nd hour after the start of the reaction were analyzed and the results are shown in Table 3.

TABLE 3

(Example 5)

| Sampling Time (Hours from start) | BP (wt %) | EBP (wt %) | | | | DiEBP (wt %) | TrEBP (wt %) | TeEBP (wt %) | 9-MF (wt %) | Others (wt %) | Total (wt %) |
|---|---|---|---|---|---|---|---|---|---|---|---|
|  |  | ortho | meta | para | Subtotal |  |  |  |  |  |  |
| 24~32 h | 12.3 | 0.8 | 18.3 | 15.8 | 34.9 | 35.7 | 11.7 | 1.2 | 3.0 | 1.2 | 100 |
| 64~72 h | 12.6 | 0.8 | 18.1 | 17.5 | 36.4 | 33.9 | 11.4 | 3.8 | 0.8 | 100 |  |

DETAILED DESCRIPTION OF THE PREFERRED EMBODIMENTS

This invention is explained with reference to the accompanying examples.

EXAMPLES 1~4

Biphenyl (BP), polyethylbenzenes (PEB), and a silica-alumina catalyst (0.46 mole per kg of acid sites with heat of adsorption of ammonia of 8.5 kilojoules per mole or more) were introduced into a pressure reactor equipped with a stirrer and allowed to react under the conditions shown in Table 1. After completion of the reaction, the reaction mixture was filtered to separate the silica-alumina catalyst from the reaction products. The composition by weight of the compounds contain-

EXAMPLE 6

Into a pressure reactor equipped with a stirrer were introduced 55 g (0.38 mole) of biphenyl (BP), 95 g (0.71 mole) of a mixture of diethylbenzene isomers (DiEB), and 45 g of the silica-alumina catalyst, the same as the one used in Example 1, and the transethylation reaction was carried out at an ethyl groups to aromatic groups mole ratio of 1.33 and at a catalyst to oil weight ratio of 0.30 by heating the mixture to 350° C. over a period of 105 minutes and maintaining the temperature at this level thereafter. Sampling was made periodically to analyze the reaction mixture. The results are shown in Table 4.

TABLE 4

(Example 6)

| Reaction Time After Temperature Rise (min.) | 0 | 60 | 120 | 180 | 240 |
|---|---|---|---|---|---|
| BP Conversion (wt %) | 43.3 | 78.0 | 81.5 | 82.0 | 82.3 |
| Ratio of Monoethyl Isomers (%) | | | | | |
| o-EBP | 5.79 | 5.76 | 5.55 | 5.58 | 5.37 |
| m-EBP | 58.80 | 61.42 | 61.53 | 61.15 | 61.21 |
| p-EBP | 35.41 | 32.82 | 32.92 | 33.27 | 33.42 |
| Ratio of Diethyl Isomers (%) | | | | | |
| 1-DiEBP | 0.76 | 0.81 | 0.94 | 0.43 | 1.38 |
| 2-DiEBP | | 0.19 | 0.35 | 0.31 | 0.80 |
| 3-DiEBP | 6.85 | 8.17 | 9.20 | 8.23 | 8.39 |
| 4-DiEBP | 5.63 | 6.14 | 5.58 | 5.59 | 5.16 |
| 3,5-DiEBP | 14.11 | 13.50 | 12.81 | 12.91 | 12.82 |
| 3,3'-DiEBP | 30.95 | 31.66 | 32.76 | 32.70 | 32.30 |
| 3,4'-DiEBP | 33.23 | 31.81 | 30.63 | 32.02 | 31.37 |
| 4,4'-DiEBP | 8.73 | 7.73 | 7.71 | 7.80 | 7.78 |

EXAMPLE 7

As illustrated in FIG. 1, fixed-bed pressure flow reactor 1 was filled with the silica-alumina catalyst, the same as the one used in Example 1, and the product line thereafter was connected to distillation columns 2a, 2b, 2c, and 2d in series. The feeds, biphenyl 3, ehtylene 4, and polyethylbenzene 5, were charged to reactor 1 together with recycle stream 6 which is a mixture of recycle stream 6a from the top of distillation column 2b and recycle stream 6b from the top of distillation column 2d. The reaction was carried out at 300° C. and a weight hourly space velocity of 2 kg/kg.hr. The mole ratio of (ethyl groups+ethylene) to (biphenyl rings+benzene rings) was 1.16 in reactor 1.

Reaction mixture 7 flowing through the reactor and emerging from the bottom thereof was charged to distillation column 2a, and top fraction 8 and bottom fraction 9 were taken out from the top and the bottom of distillation column 2a respectively. Top fraction 8 was sent to ethylbenzene plant 10 where it is a supply source of polyethylbenzene 5.

Bottom fraction 9 was charged to distillation column 2b and recycle stream 6a mainly containing biphenyls and diethylbenzenes was withdrawn from the top while fraction 11 was withdrawn from the bottom.

Bottom fraction 11 was charged to distillation column 2c where ethylbiphenyl 12 mainly consisting of ethylbiphenyls (EBP) and diethylbiphenyls (DiEBP) was withdrawn from the top and fraction 13 mainly consisting of triethylbiphenyls (TrEBP) and tetraethylbiphenyls (TeEBP) was withdrawn from the bottom.

Fraction 13 was then charged to distillation column 2d and recycle stream 6b was taken out from the top while residue 14 was taken out from the bottom.

When triethylbiphenyl is needed as product, recycle stream 6b is withdrawn from the side of distillation column 2d and the triethylbiphenyl is taken out from the top.

The material balance in the flowsheet of FIG. 1 is shown in Table 5.

TABLE 5

(Example 7)

| Compound | Sample No. (Corresponding to No. in FIG. 1) | | | | | | | | | | | | |
|---|---|---|---|---|---|---|---|---|---|---|---|---|---|
| | 3 | 4 | 5 | 6 | 7 | 8 | 9 | 6a | 11 | 12 | 13 | 6b | 14 |
| E | | 38 | | | | | | | | | | | |
| B | | | | | 118 | 118 | | | | | | | |
| EB | | | 6 | | 268 | 268 | | | | | | | |
| DiEB | | | 507 | 122 | 126 | 126 | 4 | 122 | 122 | | | | |
| TrEB | | | 39 | 16 | 16 | | | 16 | 16 | | | | |
| TeEB | | | | 5 | 5 | | | 5 | 5 | | | | |
| Subtotal of Benzen Ring Compounds | | | 552 | 143 | 533 | 390 | | 143 | 143 | | | | |
| BP | 817 | | | 290 | 294 | | | 294 | 290 | 4 | 4 | | |
| EBP | | | | 3 | 573 | | | 573 | 3 | 570 | 570 | | |
| 9-MF | | | | | 60 | | | 60 | | 60 | 60 | | |
| DiEBP | | | | 11 | 313 | | | 313 | | 313 | 302 | 11 | 11 |
| TrEBP | | | | 180 | 189 | | | 189 | | 189 | 9 | 180 | 180 |
| TeEBP | | | | 83 | 105 | | | 105 | | 105 | | 105 | 83 | 22 |
| Others | | | | 5 | 53 | | | 53 | | 53 | 45 | 8 | 5 | 3 |
| Subtotal of Biphenyl Ring Compounds | 817 | | | 572 | 1587 | | | 1587 | 293 | 1294 | 990 | 304 | 279 | 25 |
| Total | 817 | 38 | 552 | 715 | 2120 | 390 | | 1730 | 436 | 1294 | 990 | 304 | 279 | 25 |

What is claimed is:

1. A method of making ethylbiphenyls which comprises the step of reacting a mixture consisting essentially of polyethylbenzenes with a reactant consisting essentially of biphenyl in the presence of a solid acid catalyst which is at least one member selected from the group consisting silica-alumina and Y zeolite.

2. A method according to claim 1, wherein the reaction temperature is in the range 130°–380° C.

3. A method according to claim 1, wherein the polyethylbenzenes are used in a quantity such that the ratio of ethyl groups present in the reaction mixture to the total of biphenyl rings benzene rings is in the range 0.3–4.

4. A method according to claim 1, wherein the solid acid catalyst possesses 0.1–3.0 moles of acid sites per kilogram, said acid site having a heat of adsorption of ammonia of at least 85 kilojoules per mole.

5. A method of making ethylbiphenyls which comprises the step of reacting a mixture consisting essentially of ethylene and polyethylbenzenes with a reactant consisting essentially of biphenyl in the presence of a solid acid catalyst which is at least one member selected from the group consisting of silica-alumina and Y zeolite.

6. A method according to claim 5, wherein the reaction temperature is in the range 130°–380° C.

7. A method according to claim 5, wherein the ethylene and polyethylbenzenes are used in a quantity such that the ratio of ethyl groups present in the reaction mixture to the total of biphenyl rings plus benzene rings is in the range 0.3–4.

8. A method according to claim 5, wherein the solid acid catalyst possesses 0.1–3.0 moles of acid sites per kilogram, said acid site having a heat of adsorption of ammonia of at least 85 kilojoules per mole.

9. A method of making ethylbiphenyls which comprises the steps of continuously charging a feed consisting essentially of biphenyl and polyethylbenzenes to a fixed-bed flow reactor packed with a solid acid catalyst which is at least one member selected from the group consisting of silica-alumina and Y zeolite, continuously charging the reaction mixture withdrawn from said reactor to a distillation apparatus, recovering from the distillation apparatus a fraction rich in ethylbiphenyls an diethylbiphenyls as products, and leading from the distillation apparatus back to said reactor recycled materials consisting of:
(1) a fraction rich in recovered biphenyl and diethylbenzenes and
(2) a fraction rich in triethylbiphenyls and tetraethylbiphenyls.

10. A method according to claim 9, wherein the distillation apparatus consists of plural distillation columns connected in series.

11. A method of making ethylbiphenyls which comprises the steps of continuously charging a feed consisting essentially of biphenyl and polyethylbenzenes to a fixed-bed flow reactor packed with a solid acid catalyst which is at least one member selected from the group consisting of silica-alumina and Y zeolite, continuously charging the reaction mixture withdrawn from said reactor to a distillation apparatus, recovering from the distillation apparatus a fraction rich in ethylbiphenyls, diethylbiphenyls, and triethylbiphenyls as products, and leading from the distillation apparatus back to said reactor recycled materials consisting of:
(1) a fraction rich in recovered biphenyla nd diethylbenzenes, and
(2) a fraction rich in tetraethylbiphenyls.

12. A method according to claim 11, wherein the distillation apparatus consists of plural distillation columns connected in series.

13. A method of making ethylbiphenyls which comprises the steps of a continuously charging a feed consisting essentially of biphenyl, ethylene and polyethylbenzenes to a fixed-bed flow reactor packed with a solid acid catalyst which is at least one member selected from the group consisting of silica-alumina and Y zeolite, continuously charging the reaction mixture withdrawn from said reactor to a distillation apparatus, recovering from the distillation appartatus a fraction rich in ethylbiphenyls and diethylbiphenyls as products, and leading from the distillation apparatus back to said reactor recycled materials consisting of:
(1) a fraction rich in recovered biphenyl and diethylbenzenes, and
(2) a fraction rich in triethylbiphenyls and tetraethylbiphenyls.

14. A method according to claim 13, wherein the distillation apparatus consists of plural distillation columns connected in series.

15. A method of making ethylbiphenyls which comprises the steps of continuously charging a feed consisting essentially of biphenyl, ethylene and polyethylbenzenes to a fixed-bed flow reactor packed with a solid acid catalyst which is at least one member selected from the group consisting of silica-alumina and Y zeolite, continuously charging the reaction mixture withdrawn from said reactor to a distillation apparatus, recovering from the distillation apparatus a fraction rich in ethylbiphenyls, diethylbiphenyls, and triethylbiphenyls as products, and leading from the distillation apparatus back to said reactor recycled materials consisting of:
(1) a fraction rich in recovered biphenyl and diethylbenzenes, and
(2a fraction rich in tetraethylbiphenyls.

16. A method according to claim 15, wherein the distillation apparatus consists of plural distillation columns connected in series.

* * * * *